United States Patent
Tomita et al.

(10) Patent No.: US 7,141,792 B2
(45) Date of Patent: Nov. 28, 2006

(54) RADIATION DETECTOR

(75) Inventors: Yasuhiro Tomita, Hamamatsu (JP);
Masanori Kinpara, Hamamatsu (JP);
Michiatsu Nakada, Hamamatsu (JP);
Yuji Shirayanagi, Hamamatsu (JP);
Shinjiro Matsui, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/525,196

(22) PCT Filed: Aug. 20, 2003

(86) PCT No.: PCT/JP03/10527

§ 371 (c)(1),
(2), (4) Date: Feb. 22, 2005

(87) PCT Pub. No.: WO2004/019061

PCT Pub. Date: Mar. 4, 2004

(65) Prior Publication Data

US 2005/0263707 A1     Dec. 1, 2005

(30) Foreign Application Priority Data

Aug. 21, 2002  (JP) ............... 2002-240832

(51) Int. Cl.
*G01T 1/00* (2006.01)
*G01T 1/161* (2006.01)
*G21K 1/02* (2006.01)

(52) U.S. Cl. ............... 250/336.1; 250/363.02; 250/363.1

(58) Field of Classification Search ............ 250/361 R, 250/363.02, 363.1, 370.01, 370.13, 336.1; 600/431, 436
See application file for complete search history.

(56) References Cited

U.S. PATENT DOCUMENTS

| | | | | |
|---|---|---|---|---|
| 3,789,299 A | * | 1/1974 | Aslan | 324/95 |
| 4,893,013 A | * | 1/1990 | Denen et al. | 250/336.1 |
| 5,036,201 A | | 7/1991 | Carroll et al. | |
| 5,170,055 A | * | 12/1992 | Carroll et al. | 250/336.1 |
| 5,635,710 A | * | 6/1997 | Reed et al. | 250/253 |
| 5,732,704 A | | 3/1998 | Thurston et al. | |
| 6,048,093 A | * | 4/2000 | Pompei | 374/133 |
| 6,218,669 B1 | * | 4/2001 | Call | 250/370.11 |
| 6,219,573 B1 | * | 4/2001 | Pompei | 600/474 |
| 6,236,880 B1 | | 5/2001 | Raylman et al. | |
| 2001/0013576 A1 | * | 8/2001 | Miller et al. | 250/363.02 |
| 2002/0063204 A1 | * | 5/2002 | Yarnall et al. | 250/252.1 |

FOREIGN PATENT DOCUMENTS

| | | |
|---|---|---|
| JP | 61-262675 | 11/1986 |
| JP | 63-41872 | 3/1988 |

(Continued)

*Primary Examiner*—David Porta
*Assistant Examiner*—Mark R. Gaworecki
(74) *Attorney, Agent, or Firm*—Drinker Biddle & Reath LLP

(57) ABSTRACT

A radiation detector has a main body (1), and a radiation detection probe (2) detachably attached to the distal end of the main body (1). The probe (2) includes a detection unit (3) accommodating a radiation detection element (7), a cap-shaped shield member (6) mounted to the detection unit (3) so as to cover the distal end of the detection unit (3), and a probe cover (4) accommodating the detection unit (3) and the shield member (6). A connector (10) onto which the probe (2) is adapted to be screwed is provided on the distal end of the main body (1). A collimator (6A) for collimating incident radiation is provided on the distal end of the shield member (6).

19 Claims, 16 Drawing Sheets

FOREIGN PATENT DOCUMENTS

| | | |
|---|---|---|
| JP | 5-500415 | 1/1993 |
| JP | 7-064159 | 3/1995 |
| JP | 9-140658 | 6/1997 |
| JP | 2001-208856 | 8/2001 |
| JP | 9-189770 | 7/2002 |
| JP | 2002-214353 | 7/2002 |
| WO | 99/25248 | 5/1999 |

\* cited by examiner

RADIATION DETECTOR

TECHNICAL FIELD

The present invention relates to a handheld radiation detector and, more particularly, to a radiation detector which has a replaceable radiation detection probe.

BACKGROUND ART

A handheld medical radiation detector is disclosed in U.S. Pat. No. 6,236,880 B1. This radiation detector has a probe and a probe tip detachably mounted to the distal end of the probe.

DISCLOSURE OF THE INVENTION

An object of the present invention is to provide a radiation detector which detects radiation from a place to be measured with high accuracy.

In an aspect, the present invention relates to a radiation detector comprising a main body, and a radiation detection probe detachably attached to the main body. The radiation detection probe has a detection unit including a radiation detection element, and a first terminal electrically connected to the radiation detection element. The main body has a connector to which the proximal end of the radiation detection probe is detachably mounted. The connector includes a second terminal which is detachably connected to the first terminal when the radiation detection probe is mounted to the connector. A collimator for collimating radiation is provided in the distal end portion of the radiation detection probe.

When the distal end of the radiation detection probe is directed toward a place to be measured, the radiation from the place is collimated by the collimator and then enters the radiation detection element. The radiation detection element detects the radiation to generate a detection signal corresponding to its dose. The first terminal receives the detection signal, which is in turn sent to the second terminal. The main body may have a circuit which is electrically connected to the second terminal and which processes the detection signal to determine the radiation dose. Furthermore, the main body may have a device for displaying the resulting radiation dose. Since the collimator limits the angle of incidence of radiation, the incidence of radiation from places other than the place to be measured onto the radiation detection element is prevented or suppressed. Therefore, an enhanced directivity for the detection of radiation is obtained, and therefore it is possible to detect the radiation from the place to be measured with high accuracy.

The detection unit may have an input face which transmits the radiation. The radiation detection element may be arranged so as to receive the radiation which has passed through the input face. The collimator may be an opening which faces the input face. In this case, it is not necessary to install the collimator as a single component. Thus, the number of components is reduced, thereby simplifying the structure of the radiation detector. The radiation detection probe and the detection unit may have an elongated shape which extends along the common axis. In this case, the opening as the collimator may extend along the common axis.

The radiation detection probe may further have a cap-shaped shield member which is mounted to the detection unit so as to cover the radiation detection element. The shield member is made of a material which blocks the radiation. The shield member may have a front wall facing the radiation detection element and a cylindrical side wall which extends from the edge of the front wall. The collimator may be a through-hole provided in the front wall.

The radiation detection probe may further include a cap-shaped probe cover which covers the shield member and the detection unit and is detachably mounted to the connector; and a seal ring sandwiched between the probe cover and the connector to seal the main body and the radiation detection probe when the probe cover is mounted to the connector.

To replace the radiation detection element, the probe cover is removed form the connector of the main body, and accordingly the first terminal on the radiation detection probe is separated from the second terminal on the connector. Mounting a new detection unit and a probe cover in the reverse procedures allows the radiation detection element to be replaced on a detection unit basis. Preferably, the radiation detection element is adapted to be separated from the detection unit. In this case, the radiation detection element can be replaced independently. Since the main body and the radiation detection probe are sealed by the seal ring, the radiation detector can be sterilized using a sterilizing gas such as EOG or washed in water. That is, the radiation detector has improved resistance to sterilization and anti-contamination.

The shield member may be disposed in the probe cover to allow a hollow portion of the shield member and a hollow portion of the probe cover to communicate with each other. The detection unit is fitted into these hollow portions which communicate with each other. The shield member may be either detachably provided or fixed in the probe cover.

The probe cover may have a cap-shaped first component detachably mounted to the connector, a cap-shaped second component detachably attached to the first component to accommodate and fix the shield member, and a seal ring sandwiched between the outer surface of the first component and the inner surface of the second to seal the probe cover when the second component is attached to the first component. The second component may be attached at positions variable along the axis of the probe cover. In this case, the distance between the collimator and the radiation detection element can be adjusted depending on the position of the second component. Consequently, the sensitivity of the radiation detector can be readily adjusted.

The probe cover may have an input plate facing the front wall of the shield member, and a cylindrical side wall extending from an edge of the input plate to surround the side surfaces of the shield member and the detection unit. The input plate closes an end of the opening which is the collimat. The input plate is made of a material which transmits the radiation and blocks an electromagnetic wave having an energy of 1 keV or less. Preferably, the interface between the input plate and the side wall is sealed.

The detection unit may have a casing for accommodating the radiation detection element. An opening is provided on the distal end of the casing so as to extend from an end face of the casing toward the radiation detection element. This opening may have substantially the same cross-section as that of the above-mentioned opening which is the collimator and communicate with the collimator.

The radiation detection probe may further include a cap-shaped probe cover which covers the detection unit and is detachably mounted to the connector, and a seal ring sandwiched between the probe cover and the connector to seal the main body and the radiation detection probe when the probe cover is mounted to the connector. The probe cover may be made of a material which blocks the radiation. The collimator may be an opening provided on the distal end of the probe cover so as to extend toward the radiation detection element.

An input plate for closing an end of the collimator may be provided on the distal end surface of the probe cover. The input plate may be made of a material which transmits the radiation and blocks an electromagnetic wave having an energy of 1 keV or less.

The connector may further include a support bar protruding from the distal end of the main body and being thinner than the radiation detection probe. The support bar may have a proximal end connected to the distal end of the main body and a distal end connected to the radiation detection probe. The connector may further include a slide member slidably attached to the support bar. The collimator may move along with the slide member. In this case, the distance between the collimator and the radiation detection element varies when the slide member slides relative to the support bar.

One of the first and second terminals may be a pin, and the other may be a socket into which the pin is fitted. The pin may include a plurality of pins having different fitting lengths and different polarities. The socket may include a plurality of sockets having fitting lengths and polarities corresponding to these pins. When replacing the detection unit, fitting the pins and sockets having the corresponding fitting lengths to each other reliably prevents the pins and sockets having different polarities from being fitted to each other accidentally.

In another aspect, the present invention relates to a radiation detector which includes a main body, and a radiation detection probe detachably attached to the main body. The radiation detection probe has a radiation detection element, and a first terminal electrically connected to the radiation detection element, a cylindrical element cover surrounding the radiation detection element, and a cylindrical casing for accommodating the element cover. The main body has a connector to which the proximal end of the radiation detection probe is detachably mounted. The connector includes a second terminal which is detachably connected to the first terminal when the radiation detection probe is mounted to the connector. The element cover is made of a material which blocks radiation. The radiation detection element is disposed behind the distal end of the element cover.

The portion of the element cover placed in front of the radiation detection element not only prevents the sideward radiation incidence on the radiation detection element but also limits the frontward radiation incidence. As a result, the radiation incidence from places other than the place to be measured is prevented or suppressed. Accordingly, it is possible to obtain an improved directivity in the detection of radiation, and detect the radiation from the place to be measured with high accuracy.

The radiation detector may further comprise a fastener detachably mounted to the main body to fasten the radiation detection probe to the connector. The radiation detector may further comprise a seal ring sandwiched between the fastener and the connector to seal the main body when the fastener is mounted to the connector. An input plate facing the radiation detection element may be provided on the distal end surface of the casing. The input plate may be made of a material which transmits the radiation and blocks an electromagnetic wave having an energy of 1 keV or less.

The present invention will be fully understood when taken with the following detailed descriptions and the accompanying drawings. The accompanying drawings are only illustrative, and therefore it is to be understood that the accompanying drawings are not considered to limit the present invention.

A further applicable scope of the invention will become apparent from the following detailed descriptions. However, the detailed descriptions and specific examples describe the preferred embodiments of the invention but are only illustrative thereof. It will thus become apparent to those skilled in the art from the detailed descriptions that various modifications and variations can be made without departing from the scope of the invention.

BEST MODES FOR CARRYING OUT THE INVENTION

Figure 1:
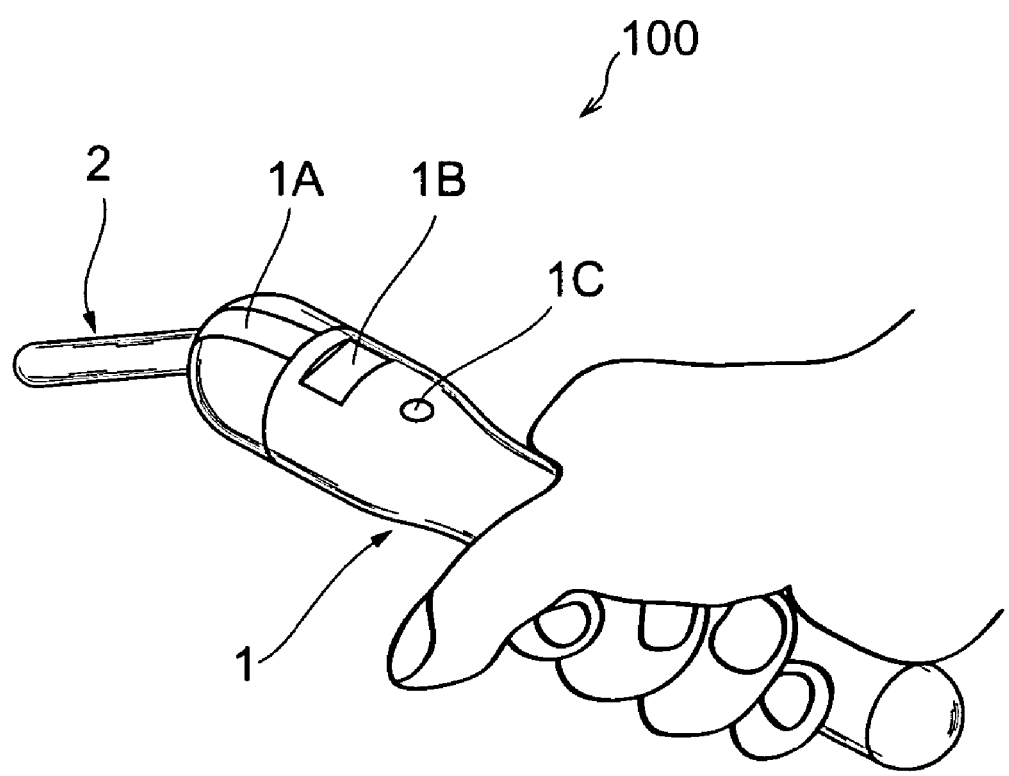
FIG. 1 is a perspective view showing a radiation detector according to a first embodiment.

Now, the present invention will be described below in more detail with reference to the accompanying drawings in accordance with the embodiments. In the drawings, identical elements are indicated by identical symbols and overlapping description will be omitted.

First Embodiment

Figure 2:
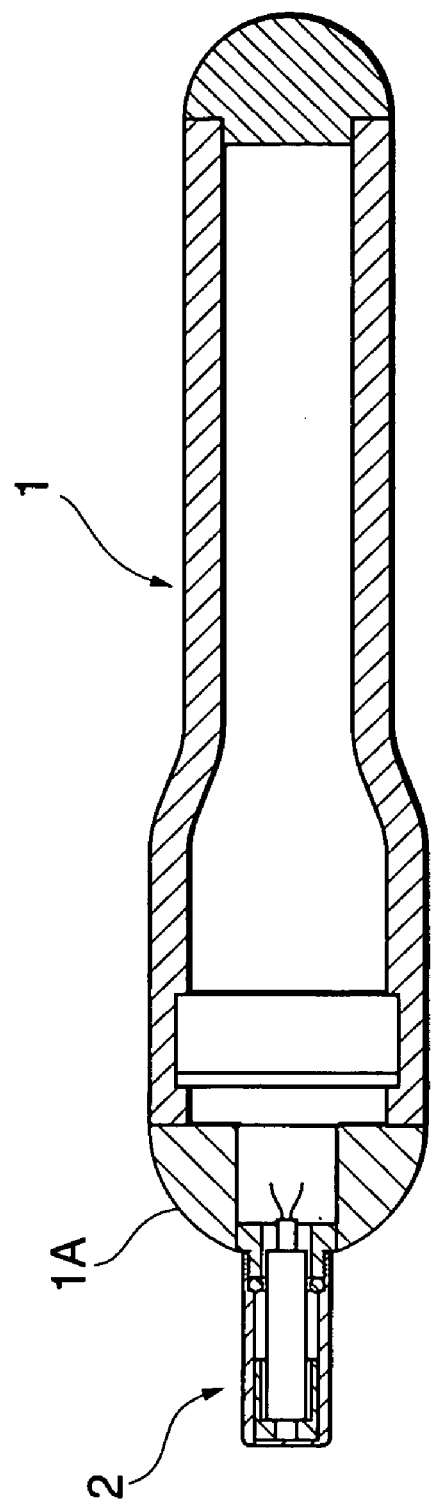
FIG. 2 is a longitudinal sectional view of the radiation detector shown in FIG. 1.
Figure 3:
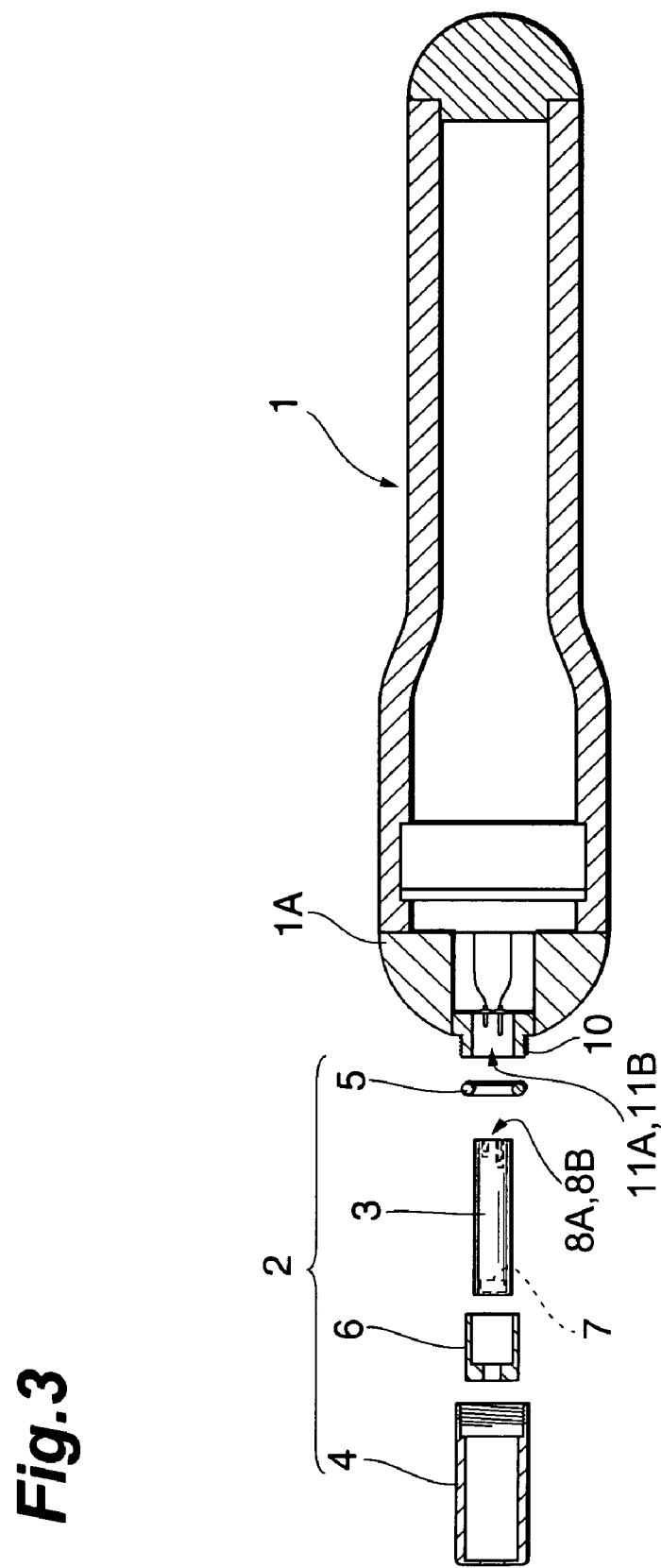
FIG. 3 is an exploded sectional view of the radiation detector shown in FIG. 2.
Figure 4:
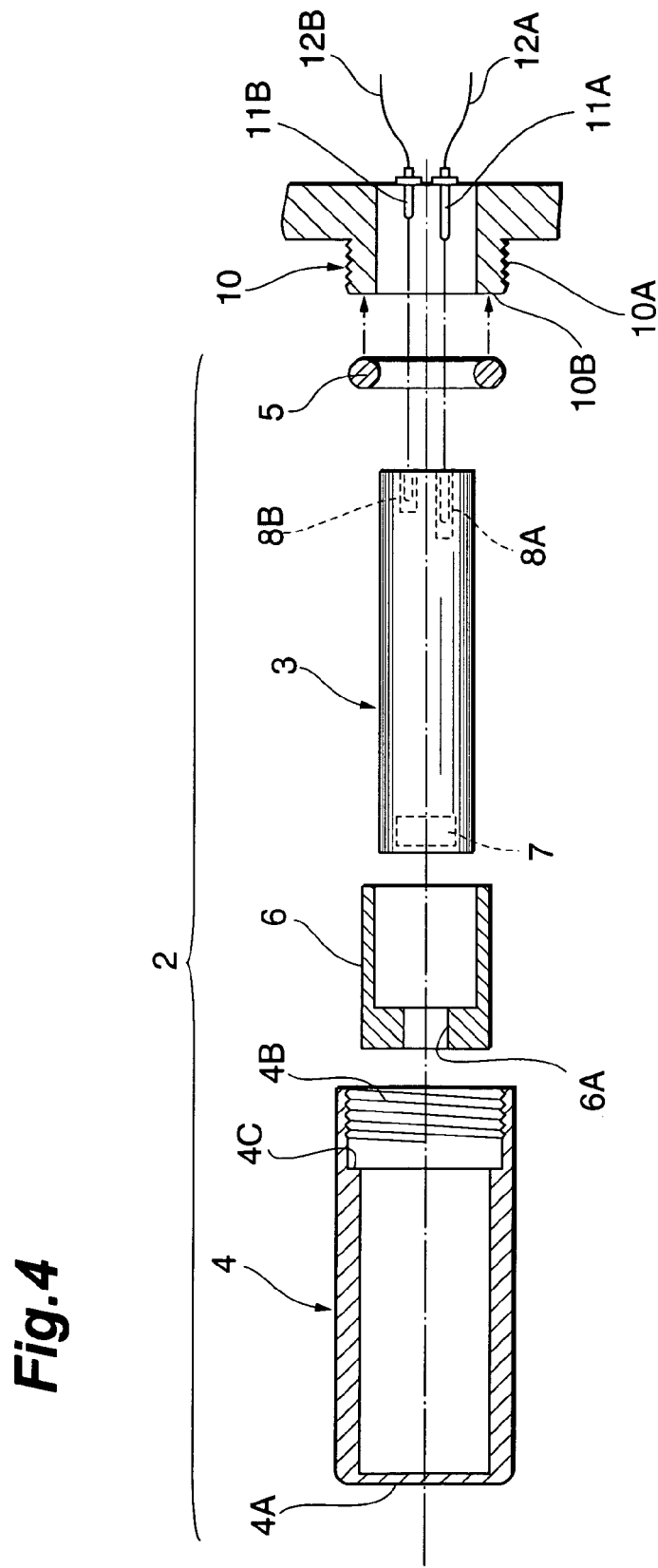
FIG. 4 is an enlarged exploded sectional view of the radiation detection probe shown in FIG. 3.
Figure 5:
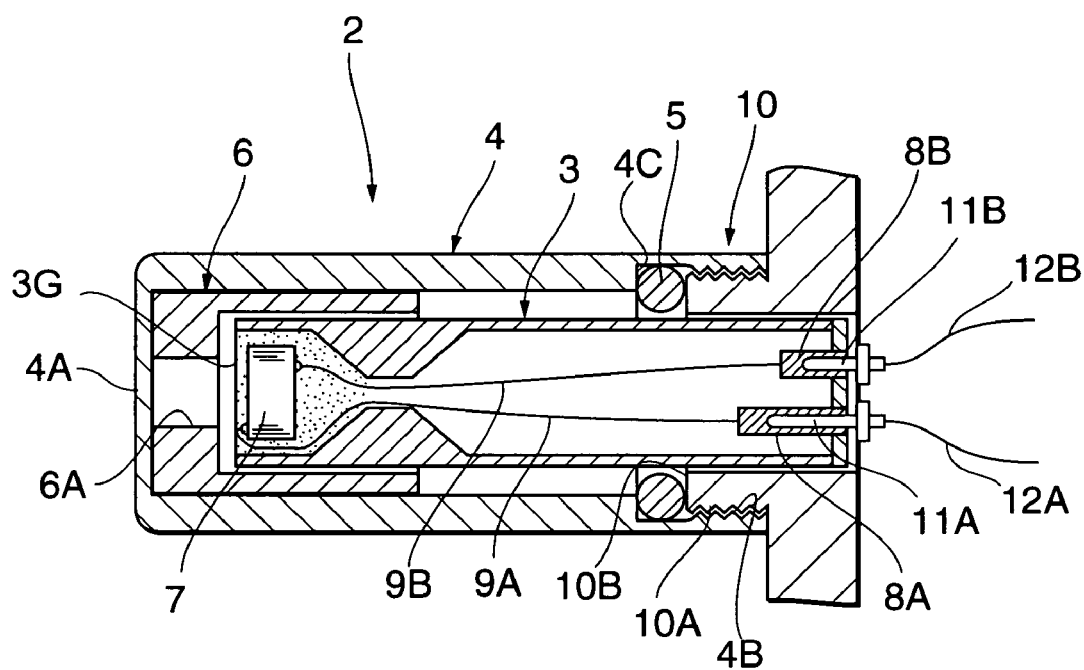
FIG. 5 is a longitudinal sectional view of the assembled radiation detection probe shown in FIG. 4.

FIG. 1 is a perspective view showing a radiation detector according to a first embodiment. FIG. 2 is a longitudinal sectional view showing the radiation detector shown in FIG. 1. FIG. 3 is an exploded sectional view showing the radiation detector shown in FIG. 2. FIG. 4 is an enlarged exploded sectional view showing the radiation detection probe shown in FIG. 3. FIG. 5 is an enlarged sectional view showing the assembled radiation detection probe.

A radiation detector 100 is a handheld, cordless, surgical probe. As shown in FIG. 1, the radiation detector 100 has a main body 1, and a radiation detection probe 2 provided at the distal end of the main body 1 so as to protrude from the main body 1. The radiation detector 100 is manipulated by grasping the main body 1. For example, the radiation detector 100 is used for detecting a metastatic breast cancer nidus using a radiative medicine. The radiation detection probe 2 is detachably mounted to a support member 1A of the main body 1. The support member 1A is pivotably supported at the distal end of the main body 1. The orientation of the probe 2 can be adjusted by rotating the support member 1A. Behind the support member 1A on the surface of the main body 1, provided are a liquid crystal display panel 1B and a switch 1C.

As shown in FIG. 2, the main body 1 is hollow. Although not shown, a signal processing circuit, a drive circuit, an electronic sound generator, a power supply circuit, a battery and the like are provided inside the main body 1. The signal processing circuit processes a detection signal sent from the radiation detection probe 2 to generate a data signal indicative of the radiation dose. The data signal is sent to the drive circuit. The drive circuit displays the radiation dose indicated by the data signal on the display panel 1B as well as drives the electronic sound generator to produce an electronic sound corresponding to the radiation dose.

As shown in FIG. 3 and FIG. 4, the radiation detection probe 2 has a detection unit 3, a probe cover 4, a seal ring 5, and a side shield 6. As shown in FIG. 5, the seal ring 5 and the side shield 6 are disposed so as to surround the outer circumference surface of the detection unit 3. The probe cover 4 covers the detection unit 3, the seal ring 5, and the side shield 6. The radiation detection probe 2 and the detection unit 3 have elongated shapes which have a common axis.

Figure 6:
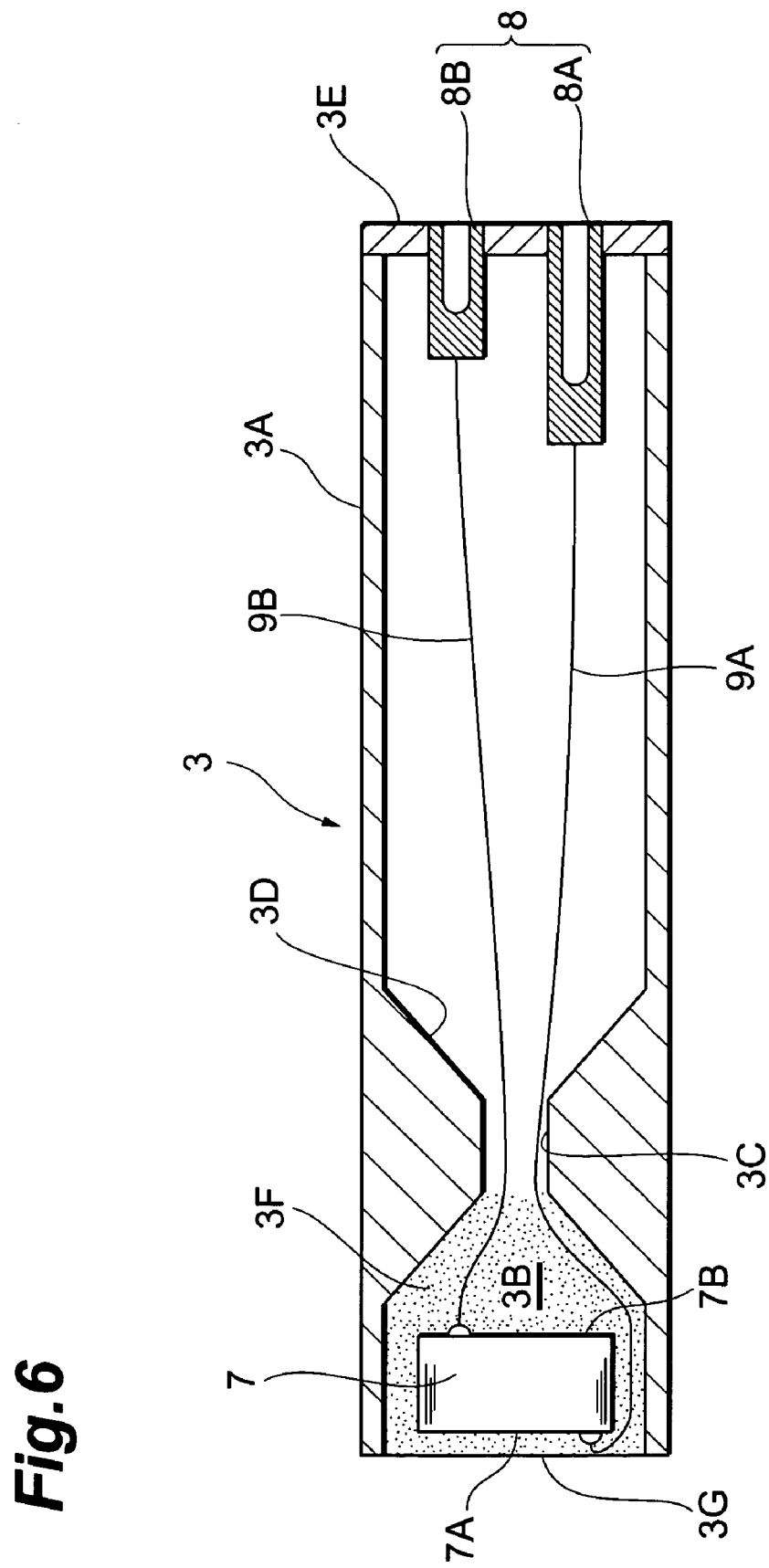
FIG. 6 is an enlarged sectional view of the radiation detection probe shown in FIG. 4.

As shown in FIG. 6, the detection unit 3 has an approximately cylindrical casing 3A. A radiation detection element 7 is disposed inside the distal end of the casing 3A. The radiation detection element 7 has a front face 7A serving as a detecting face to receive radiation and a rear face 7B placed opposite the front face 7A. A coupler 8 for the radiation detection element 7 is provided in the proximal end of the casing 3A. Behind the radiation detection element 7 inside the casing 3A, a partition 3D having a through-hole 3C is formed to define an accommodating portion 3B of the radiation detection element 7. A circular support plate 3E for holding the coupler 8 is fixed on the proximal end of the casing 3A.

For example, the casing 3A is made of a resin material such as polyoxymethylene or an electrically conductive metal material. The casing 3A may be composed either of a material which transmits the radiation to be detected or a material which blocks the radiation to be detected. An electrically insulating adhesive 3F such as a silicone resin is filled in the accommodating portion 3B to fix the radiation detection element 7 with its front face 7A facing the distal end of the casing 3A. As the coupler 8, a socket 8A having a longer fitting length and a socket 8B having a shorter fitting length are fixed to the support plate 3E, with the sockets passing through the support plate 3E. The socket 8A having the longer fitting length is connected to the front face 7A of the radiation detection element 7 via a lead wire 9A inserted through the through-hole 3C. The socket 8B having the shorter fitting length is connected to the rear face 7B of the radiation detection element 7 via a lead wire 9B inserted through the through-hole 3C. The detection unit 3 has an input face 3G placed opposite the front face 7A of the detection element 7. The radiation passes through the input face 3G to enter the front face 7A of the detection element 7.

The radiation detection element 7 is a semiconductor element which generates a voltage pulse having a pulse height corresponding to the energy of the radiation photon. The detection element 7 may be replaced by a combination of a scintillator which emits light when illuminated with radiation and a photoelectric converter. The scintillator is made of rare-earth oxides such as $CdWO_4$. For example, the photoelectric converter has a structure in which a TFT (Thin Film Transistor) is overlaid on a photodiode.

Figure 7:
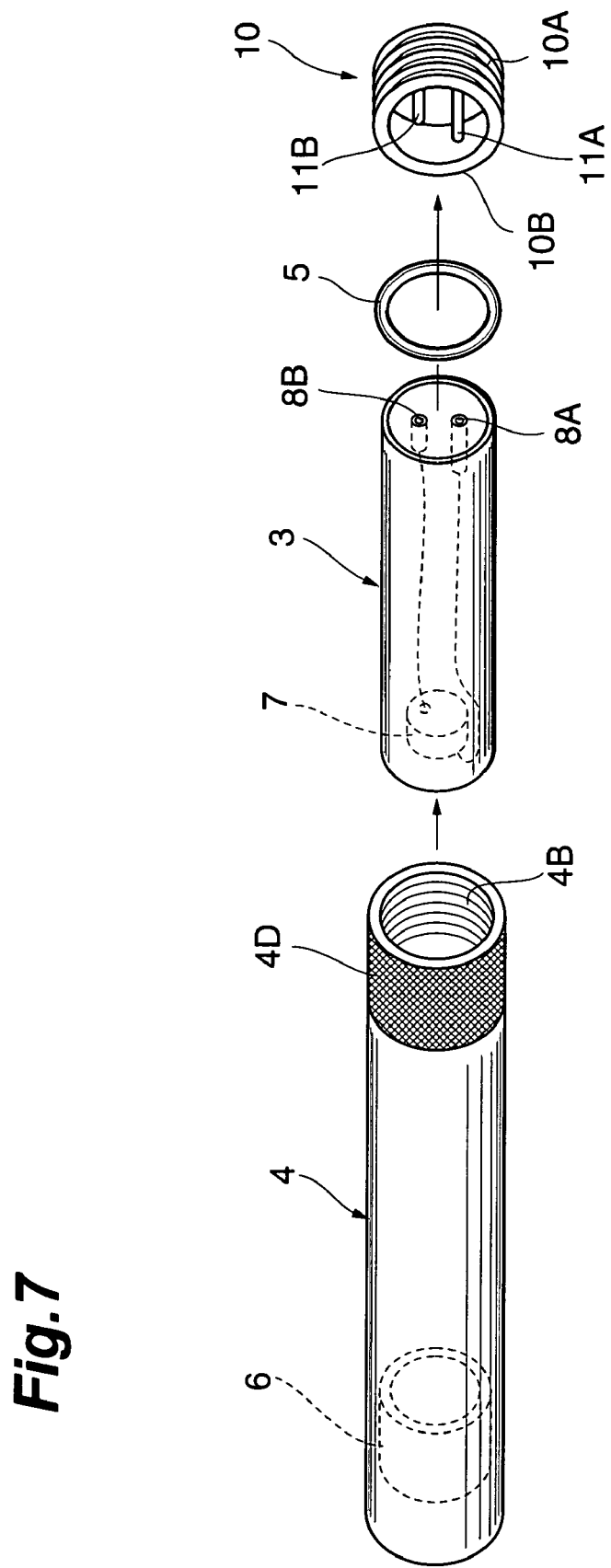
FIG. 7 is an exploded perspective view of showing the components of the radiation detection probe shown in FIG. 4, when viewed from the proximal end side of the radiation detection probe.
Figure 8:
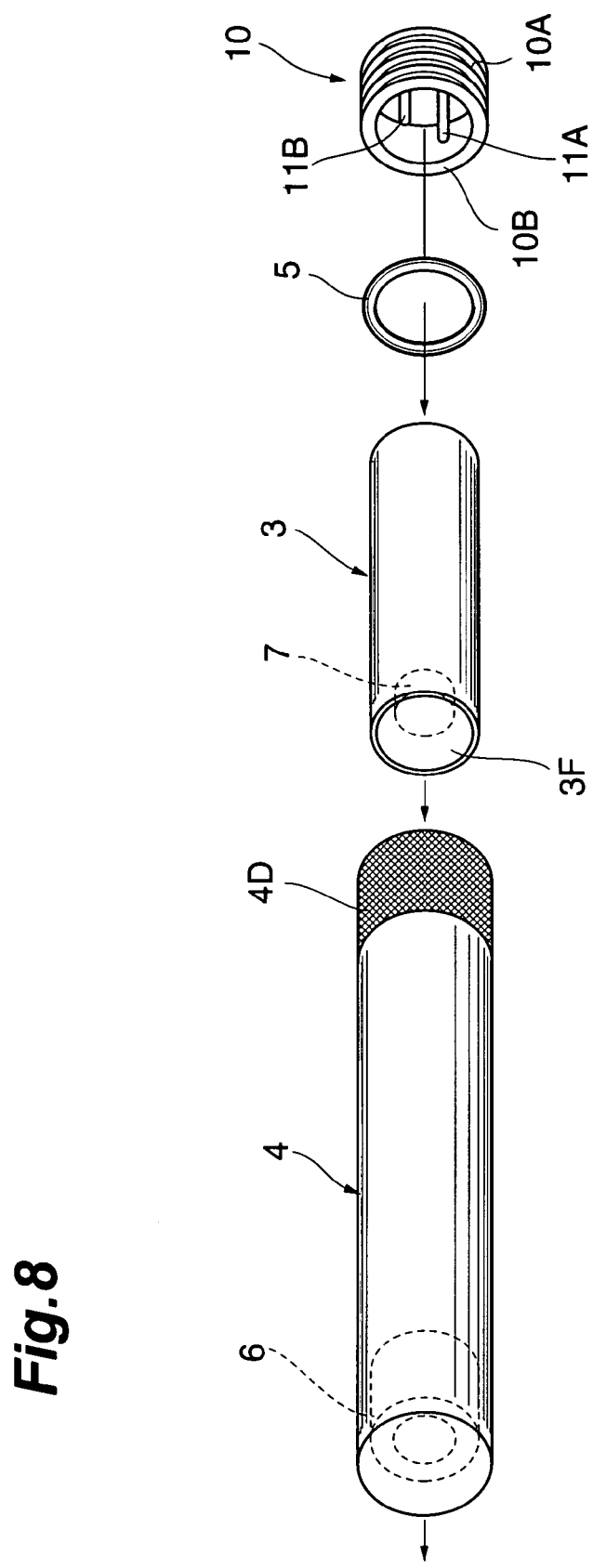
FIG. 8 is an exploded perspective view showing the components of the radiation detection probe shown in FIG. 4, when viewed from the distal end side of the radiation detection probe.

As shown in FIG. 4 and FIG. 5, the probe cover 4 is formed in the shape of a cylindrical cap so as to cover the detection unit 3 and the side shield 6. In this embodiment, the probe cover 4 is made of a material which transmits radiation. An example of this material includes a metal material such as stainless steel or aluminum or an electrically conductive resin material. A front wall 4A disposed on the distal end of the probe cover 4 is reduced in thickness to readily transmit the radiation. An internal thread 4B used to mount the probe 2 onto the main body 1 and an annular shoulder portion 4C for accommodating the seal ring 5 are formed on the inner surface of the proximal end portion of the probe cover 4. The annular shoulder portion 4C is disposed adjacent to the distal end of the internal thread 4B. As shown in FIG. 7 and FIG. 8, on the outer circumferential surface at the proximal end of the probe cover 4, formed is a knurl 4D for screwing operations.

The side shield 6 is a component for enhancing the directivity in the detection of radiation. The side shield 6 is made of a material which is capable of blocking the radiation, e.g., lead (Pb) or tungsten (W). This material may be coated with rubber. As shown in FIG. 4 and FIG. 5, the side shield 6 is an approximately cylindrical member which fits into the hollow portion of the probe cover 4. The side shield 6 covers the distal end portion of the detection unit 3. The hollow portion of the side shield 6 engages with the detection unit 3. The front wall disposed on the distal end of the side shield 6 is provided with a radiation-introducing window 6A with a small diameter which window faces the radiation detection element 7 in the detection unit 3. The window 6A is a cylindrical opening which extends coaxially with the side shield 6. The radiation passes through the window 6A to enter the radiation detection element 7.

Since the side surface of the radiation detection element 7 is covered with the side shield 6, the radiation from the side of the radiation detection element 7 is prevented from entering the radiation detection element 7. As a result, only the radiation from the direction in which the radiation detection probe 2 is directed is detected, whereby the directivity in the detection of radiation is improved. Furthermore, the side shield 6, which has the window 6A, also serves as a collimator for the radiation. The window 6A is formed coaxial with the side shield 6, thereby allowing only such radiation as traveling approximately in parallel to the axis of the window 6A and the side shield 6 to enter the radiation detection element 7. This is the collimating operation of the window 6A. Such an operation of the collimator will further improve the directivity in the detection of radiation.

As shown in FIG. 2 and FIG. 3, the radiation detection probe 2 is detachably mounted to the distal end of the main body 1. The support member 1A disposed at the distal end of the main body 1 has a connector 10, to which the radiation detection probe 2 is detachably mounted. The connector 10 is a cylindrical body which protrudes from the middle of the support member 1A. The connector 10 extends coaxially with the main body 1. The opening of the connector 10 fits detachably over the detection unit 3.

As shown in FIG. 4 and FIG. 5, the outer circumferential surface of the connector 10 is formed with an external thread 10A which screws into the internal thread 4B of the probe cover 4. This makes it possible to screw the probe cover 4 over the connector 10. The seal ring 5 is supportably sandwiched between a distal end surface 10B of the connector 10 and the annular shoulder portion 4C of the probe cover 4. In the connector 10, a terminal pin 11A having a longer fitting length and a terminal pin 11B having a shorter fitting length are disposed in parallel to the connector 10. The terminal pins 11A and 11B are electrically connected to a signal processing circuit (not shown) inside the main body 1 via lead wires 12A and 12B.

As shown in FIG. 4 and FIG. 7, to mount the radiation detection probe 2 to the distal end of the main body 1, the detection unit 3 is first inserted into the connector 10 of the main body 1 to insert the terminal pins 11A and 11B into the sockets 8A and 8B. The terminal pin 11A having the longer fitting length and the socket 8A having the longer fitting length are connected together, while the terminal pin 11B having the shorter fitting length and the socket 8B having the shorter fitting length are connected together. This makes it possible to reliably prevent a terminal pin and a socket which have different polarities from being accidentally connected together.

Thereafter, the seal ring 5 is mounted onto the outer circumference surface of the detection unit 3 so as to abut the distal end surface 10B of the connector 10, while the side shield 6 is fitted into the distal end portion of the probe cover 4. Subsequently, the detection unit 3 is inserted into the probe cover 4 so that the internal thread 4B at the proximal end of the probe cover 4 is engaged with the external thread 10A of the connector 10. This simple procedures allows the cap-shaped probe cover 4 to cover the side shield 6 and the detection unit 3, as shown in FIG. 5, and to be mounted onto the connector 10. The seal ring 5 is sandwiched between the distal end surface 10B of the connector 10 and the annular shoulder portion 4C of the probe cover 4, thereby allowing the main body 1 and the probe 2 to be sealed.

For example, the radiation detector 100 having the radiation detection probe 2 mounted thereto is used for detecting a metastatic breast cancer nidus using a radiative medicine. In this case, the radiation detection probe 2, which directly contacts the patient skin, may be sterilized using a sterilizing gas such as ethylene oxide gas (hereinafter referred to as "EOG") or washed in water. Since the radiation detection probe 2 is sealed by the seal ring 5, no problem will be raised in the sterilization or washing.

On the other hand, the radiation detector 100 described in U.S. Pat. No. 6,236,880 B1 does not have such a structure that seals a probe chip containing a radiation detection unit therein. Accordingly, when the probe distal end is sterilized using a gas such as EOG, the gas may intrude into the probe chip to have an adverse effect on the radiation detection element or its signal transmitting system. It is also difficult to wash a contaminated probe chip in water.

The operation of the radiation detector 100 will now be described below. During use of the radiation detector 100, the distal end of the radiation detection probe 2 is directed to a portion to be measured of a patient. The radiation coming from the portion to be measured passes through the front wall 4A of the probe cover 4 and the radiation-introducing window 6A of the side shield 6 to enter the radiation detection element 7. The side shield 6 and the window 6A block the radiation from portions other than the portion to be measured. This makes it possible to detect the dose of the radiation from the portion to be measured with high accuracy. The detection element 7 generates a detection signal corresponding to the radiation dose. This detection signal is sent to the signal processing circuit (not shown) in the main body 1 via the lead wires 9A and 9B, the sockets 8A and 8B, the terminal pins 11A and 11B, and the lead wires 12A and 12B. As a result, the data signal indicative of the radiation dose is generated, and the radiation dose is displayed on the liquid crystal display panel 1B. Also, the electronic sound is generated corresponding to the radiation dose.

As shown in FIG. 4 and FIG. 8, to replace the radiation detection element 7, procedures reverse to the above-mentioned procedures are followed to remove the probe cover 4 by rotating it in the direction reverse to that in which it is screwed onto the connector 10. Thereafter, the terminal pins 11A and 11B are withdrawn from the sockets 8A and 8B of the detection unit 3 to remove the detection unit 3. Then, the terminal pins 11A and 11B of a new detection unit 3 are inserted into the sockets 8A and 8B of the detection unit 3 to mount the detection unit 3. Thereafter, the above-mentioned procedure is followed to mount the probe cover 4 to the connector 10 along with the seal ring 5. This simple procedure makes it possible to replace the radiation detection element 7 on detection unit 3 basis.

Since the side shield 6 can be separated from the probe cover 4 (see FIG. 4), the probe cover 4 can be removed from the connector 10, thereby allowing the side shield 6 to be easily replaced. Thus, a plurality of side shields with a radiation-introducing window 6A having a different length and diameter can be replaced for use, thereby facilitating the adjustment of the sensitivity of the radiation detection element 7.

Second Embodiment

Figure 9:
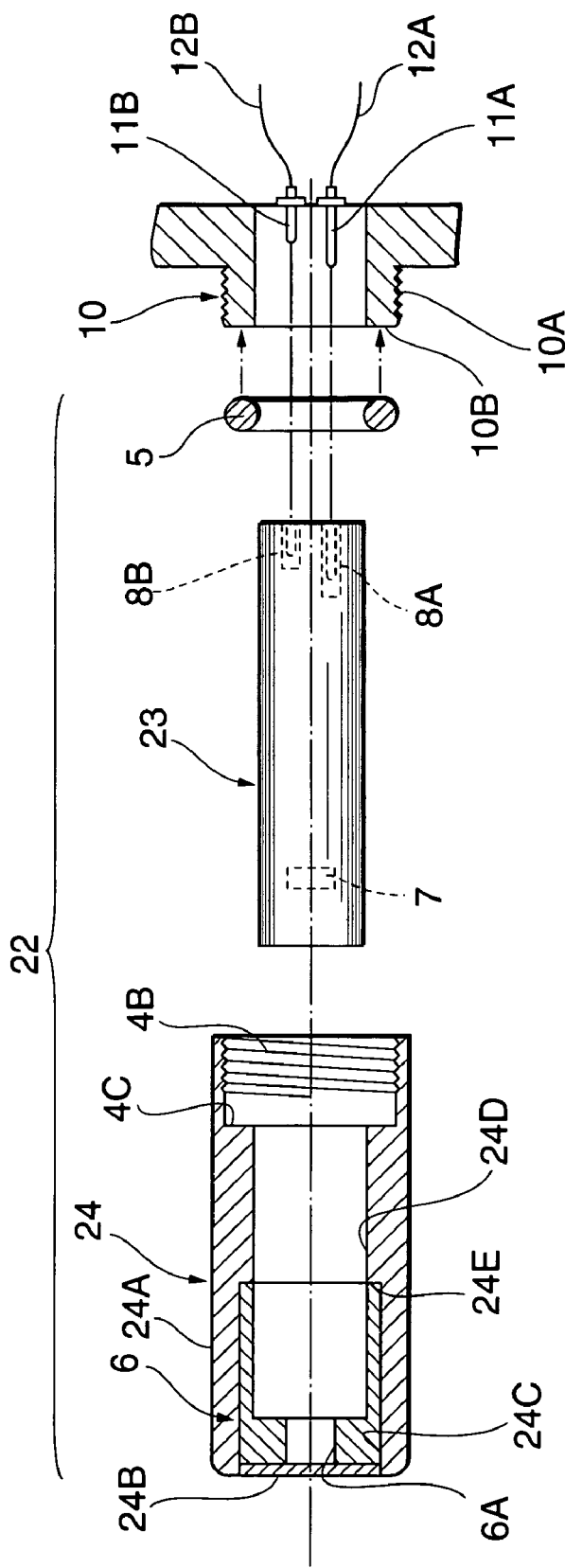
FIG. 9 is an enlarged exploded sectional view showing the radiation detection probe according to a second embodiment.
Figure 10:
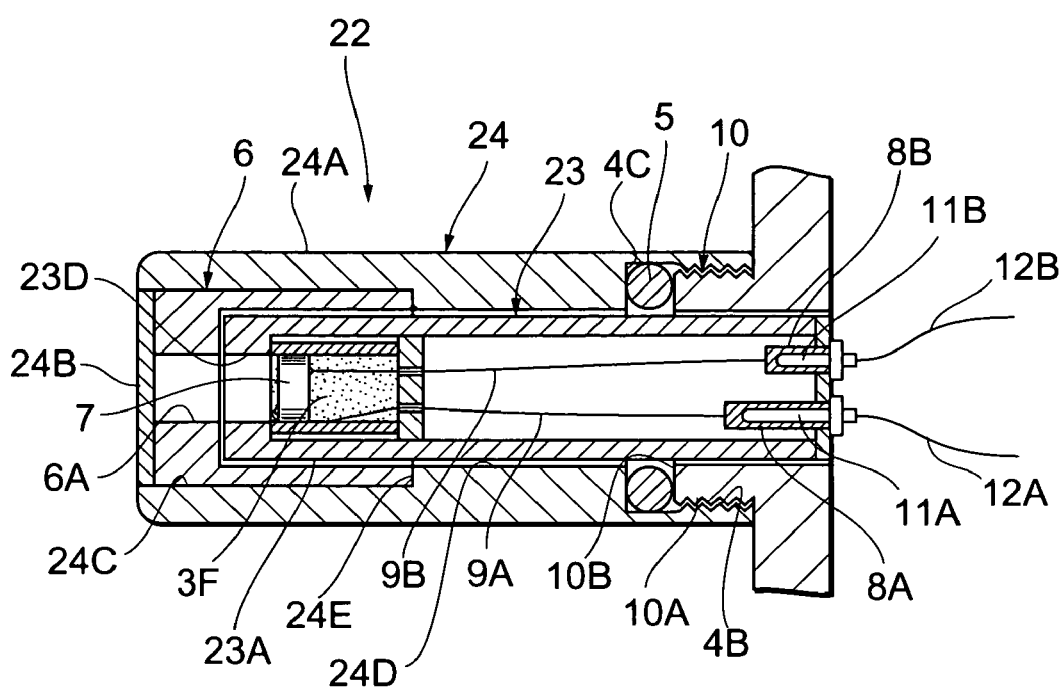
FIG. 10 is an enlarged sectional view of the assembled radiation detection probe shown in FIG. 9.
Figure 11:
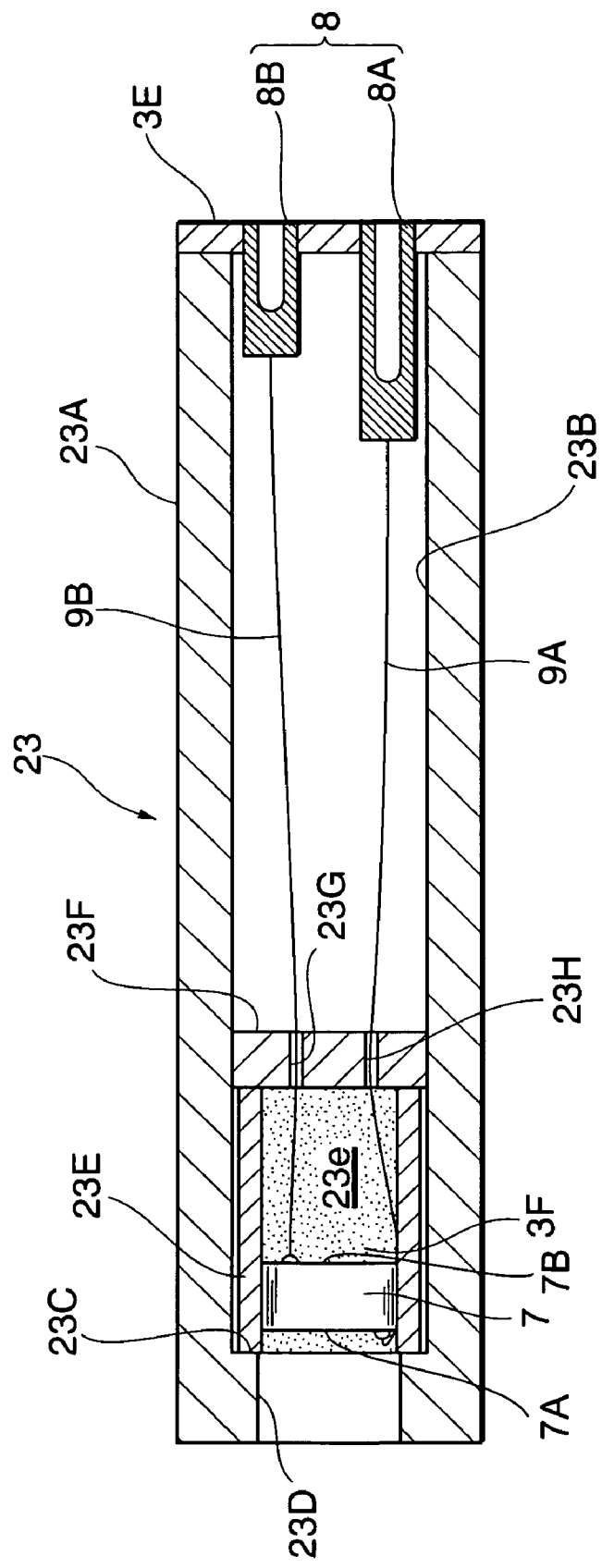
FIG. 11 is an enlarged sectional view of the detection unit shown in FIG. 9.

FIG. 9 to FIG. 11 show the main portion of a radiation detector according to a second embodiment. The second embodiment is different from the first embodiment in the fixing structure of the radiation detection element to be built in the detection unit and the fixing structure for fixing the side shield to the probe cover. Except for these structures, the second embodiment is configured in the same manner as the first embodiment.

As shown in FIG. 9 and FIG. 10, the radiation detector according to this embodiment has a structure in which the radiation detection probe 2 according to the first embodiment is replaced by a radiation detection probe 22. The radiation detection probe 22 has a detection unit 23, a probe cover 24, the seal ring 5, and the side shield 6. As shown in FIG. 11, the detection unit 23 includes the radiation detection element 7 at the distal end portion of an approximately cylindrical casing 23A. The casing 23A is made of the same material as that of the casing 3A according to the first embodiment. The casing 23A may also be made of a material which transmits the radiation to be detected or of a material which blocks the radiation to be detected. The hollow portion of the casing 23A includes an increased diameter portion 23B having a larger diameter and a reduced diameter portion 23D having a smaller diameter. The increased diameter portion 23B and the reduced diameter portion 23D form a continuous portion via an annular shoulder portion 23C. The reduced diameter portion 23D is located at the distal end of the casing 23A, and is an opening which extends from the distal end surface of the detection unit 23 toward the radiation detection element 7.

The casing 23A includes therein a cylindrical element cover 23E and a fixture member 23F. In this embodiment, the element cover 23E is made of resin, and surrounds and contacts the radiation detection element 7. The element cover 23E may be made of metal, and in this case, the radiation detection element 7 is disposed so as not to contact the detection unit 23. The element cover 23E is fitted into the increased diameter portion 23B with an end thereof being in contact with the annular shoulder portion 23C. The fixture member 23F is fitted into the increased diameter portion 23B so as to abut the other end of the element cover 23E, thereby latching the element cover 23E. Inside the hollow portion 23e of the element cover 23E, the radiation detection element 7 is fixed with its front face (detecting face) 7A being oriented toward the distal end of the element cover 23E. Also, the hollow portion 23e is filled with an electrically insulating adhesive 3F, such as a silicone resin. The lead wires 9A and 9B connected to the front face 7A and rear face 7B of the radiation detection element 7 are connected to the sockets 8A and 8B via through-holes 23G and 23H which are formed in the fixture member 23F.

The probe cover 24 has a cylindrical cap-shaped seal structure for covering the detection unit 23. As shown in FIG. 9, the probe cover 24 has a cylindrical body 24A, and an input plate 24B fitted into the opening at the distal end of the cylindrical body 24A. The input plate 24B is fixed to the cylindrical body 24A using an adhesive or the like while the cylindrical body 24A being sealed. The cylindrical body 24A may be made of either a material which transmits the radiation to be detected or a material which blocks the radiation to be detected. The input plate 24B is made of a material which blocks visible and infrared light but transmits the radiation to be detected, e.g., aluminum or amorphous carbon. This is because incidence of electromagnetic waves other than the radiation to be detected upon the radiation detection element 7 generates noise signals. Preferably, the input plate 24B is made of a material which blocks electromagnetic waves having an energy of 1 keV or less but transmits the radiation to be detected.

The hollow portion of the cylindrical body 24A includes an increased diameter portion 24C having a larger diameter and a reduced diameter portion 24D having a smaller diameter. The side shield 6 is inserted from the distal end of the cylindrical body 24A into the increased diameter portion 24C and fixed therein, and also the input plate 24B is fixed in the increased diameter portion 24C to seal it. The reduced diameter portion 24D has such a diameter that allows the detection unit 23 to be fitted therein. An annular shoulder portion 24E is provided between the reduced diameter portion 24D and the increased diameter portion 24C so as to abut the proximal end face of the side shield 6. As shown in FIG. 10, the radiation-introducing window 6A of the side shield 6 which is fitted into the increased diameter portion 24C communicates with the reduced diameter portion 23D of the casing 23 to face the radiation detection element 7. The window 6A and the reduced diameter portion 23D have substantially the same cross-section.

Like the first embodiment, before using the radiation detector according to the second embodiment, the radiation detection probe 22 may be sterilized using a sterilizing gas such as EOG or washed in water. During the operation of the radiation detector, the high directivity of the radiation detection probe 22 makes it possible to detect the dose of the radiation from the portion to be measured with high accuracy. Furthermore, the radiation detection element 7 of the radiation detection probe 22 can be replaced on a detection unit 23 basis as necessary. In this case, the installation of the side shield 6 is not necessary because the side shield 6 is integrally fixed to the probe cover 24.

Third Embodiment

Figure 12:
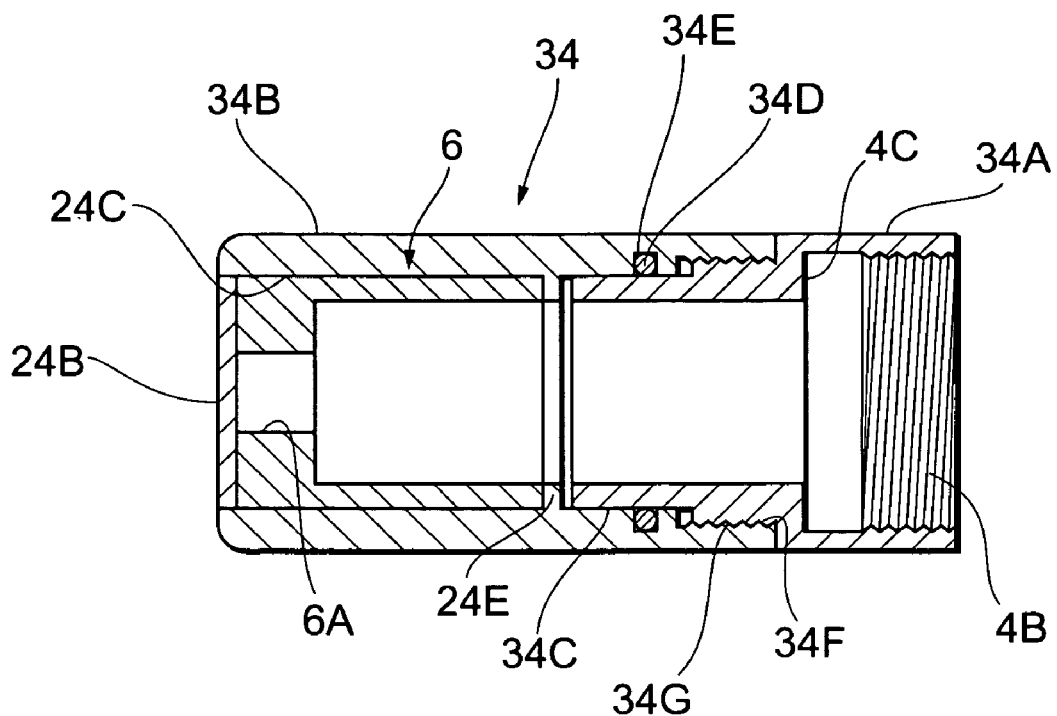
FIG. 12 is an enlarged sectional view showing a probe cover according to a third embodiment.

The third embodiment is different from the second embodiment in the structure of the probe cover, and the other structures are configured in the same manner as in the second embodiment. That is, the radiation detector according to this embodiment is configured such that the probe cover 24 (see FIG. 9) according to the second embodiment is replaced by a probe cover 34 shown in FIG. 12.

In the probe cover 34, the portion corresponding to the cylindrical body 24A shown in FIG. 9 is divided into a proximal end cover 34A and a distal end cover 34B, which can be fastened to each other. These covers 34A and 34B are formed cylindrically to have a common axis. The covers 34A and 34B may be made of either a material which transmits the radiation to be detected or a material which blocks the radiation to be detected. The proximal end cover 34A has the internal thread 4B to be fastened to the connector 10 of the main body 1. The distal end cover 34B integrally includes the side shield 6. When the proximal end cover 34A is fastened to the distal end cover 34B, the outer surfaces of the covers 34A and 34B are flush with each other.

A fitting portion 34C is provided at the distal end of the proximal end cover 34A. The fitting portion 34C has an outer diameter smaller than the distal end cover 34B, and protrudes into the hollow portion of the distal end cover 34B to be slidably fitted in the distal end cover 34B. On the inner circumference surface of the distal end cover 34B, a mount groove 34E for a seal ring 34D is annually formed. For example, the seal ring 34D is an O-ring, and seals between the inner surface of the distal end cover 34B and the outer surface of the fitting portion 34C. An internal thread 34F having a diameter larger than that of the outer surface of the fitting portion 34C is formed on the inner surface of the proximal end of the distal end cover 34B. An external thread 34G to engage with the internal thread 34F is formed at the middle of the proximal end cover 34A.

It is possible to adjust the position of the distal end cover 34B relative to the proximal end cover 34A along the axis of the probe cover 34 depending on the amount of screwing the internal thread 34F onto the external thread 34G. The distal end cover 34B has the side shield 6 integrally built therein. This allows the side shield 6 to be readily placed closer to or farther away from the radiation detection element 7 in the detection unit 23, thereby facilitating the adjustment of the sensitivity of the radiation detection element 7.

Fourth Embodiment

Figure 13:
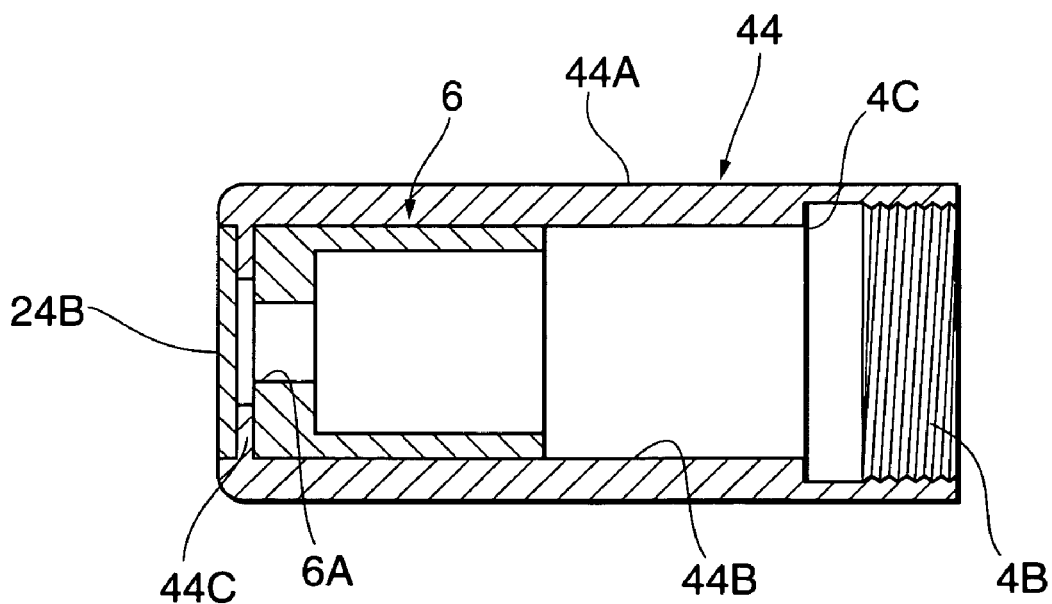
FIG. 13 is an enlarged sectional view showing a probe cover according to a fourth embodiment.

The fourth embodiment is different from the second embodiment in the structure of the probe cover, and the other structures are configured in the same manner as in the second embodiment. That is, the radiation detector according to this embodiment is configured such that the probe cover 24 (see FIG. 9) according to the second embodiment is replaced by a probe cover 44 shown in FIG. 13.

The probe cover 44 has the input plate 24B secured at the distal end of the probe cover 44 and a cylindrical body 44A extending from the edge of the input plate 24B. The cylindrical body 44A may be made of either a material which transmits the radiation to be detected or a material which blocks the radiation to be detected. The interface between the input plate 24B and the cylindrical body 44A is sealed. The side shield 6 can be detachably fitted into the hollow portion of the cylindrical body 44A. Unlike the above-mentioned embodiments, the side shield 6 is inserted from the proximal end of the probe cover 44 in this embodiment. An annular projection 44C is formed on the inner surface of the distal end of the cylindrical body 44A behind the input plate 24B. The annular projection 44C latches the distal end surface of the side shield 6.

In this embodiment, the side shield 6 is detachably housed in the cylindrical body 44A. Accordingly, by removing the probe cover 44 from the connector 10, the side shield 6 can be easily replaced. Thus, a plurality of side shields having a radiation-introducing window 6A with a different length and diameter can be replaced for use, thereby facilitating the adjustment of the sensitivity of the radiation detection element.

Fifth Embodiment

Figure 14:
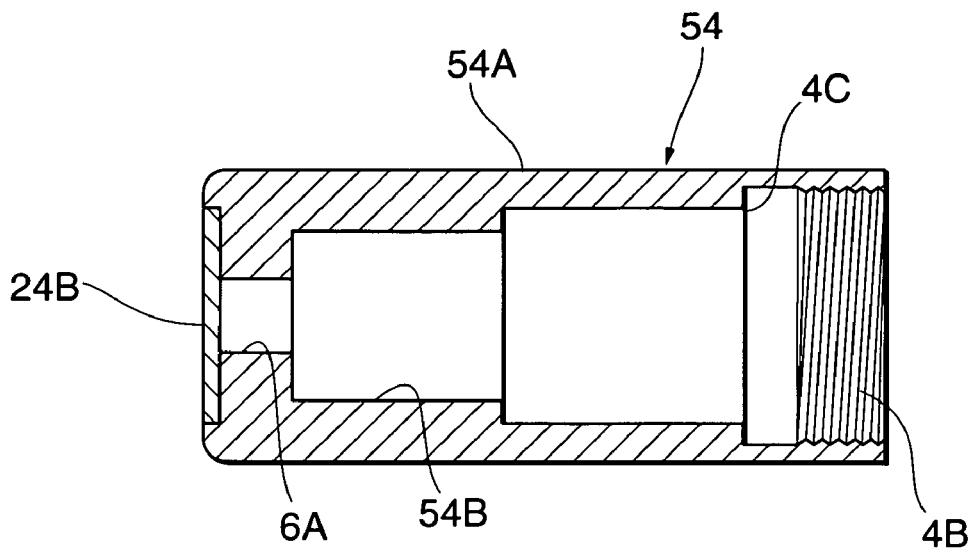
FIG. 14 is an enlarged sectional view showing a probe cover according to a fifth embodiment.

The fifth embodiment is different from the second embodiment in the structure of the probe cover, and the other structures are configured in the same manner as in the second embodiment. That is, the radiation detector according to this embodiment is configured such that the probe cover 24 (see FIG. 9) according to the second embodiment is replaced by a probe cover 54 shown in FIG. 14.

The probe cover 54 has the input plate 24B secured at the distal end of the probe cover 54 and a cylindrical body 54A extending from the edge of the input plate 24B. The interface between the input plate 24B and the cylindrical body 54A is sealed. The cylindrical body 54A is made of a material, e.g., lead (Pb) or tungsten (W), which can block the radiation, and serves as a side shield and a collimator. The radiation-introducing window 6A facing the input plate 24B is formed at the distal end of the cylindrical body 54A. The window 6A serves to collimate the radiation. Furthermore, a unit accommodating portion 54B which communicates with the window 6A is formed in the cylindrical body 54A. The distal end portion of the detection unit 23 can be detachably fitted into the unit accommodating portion 54B.

Since the cylindrical body 54A serves as a side shield and a collimator, the side shield 6 as a single component can be eliminated. This allows the number of components to be reduced, thereby simplifying the structure of the radiation detector. Also, the probe cover 54 can be removed from the connector 10, thereby allowing the detection unit 23 to be readily replaced.

Furthermore, since the probe cover 54 can block the radiation by itself, it is possible to improve the capability of blocking sideward radiation without increasing the diameter of the radiation detection probe 22, or reduce the diameter of the radiation detection probe 22 while approximately keeping the same capability of blocking radiation.

Sixth Embodiment

Figure 15:
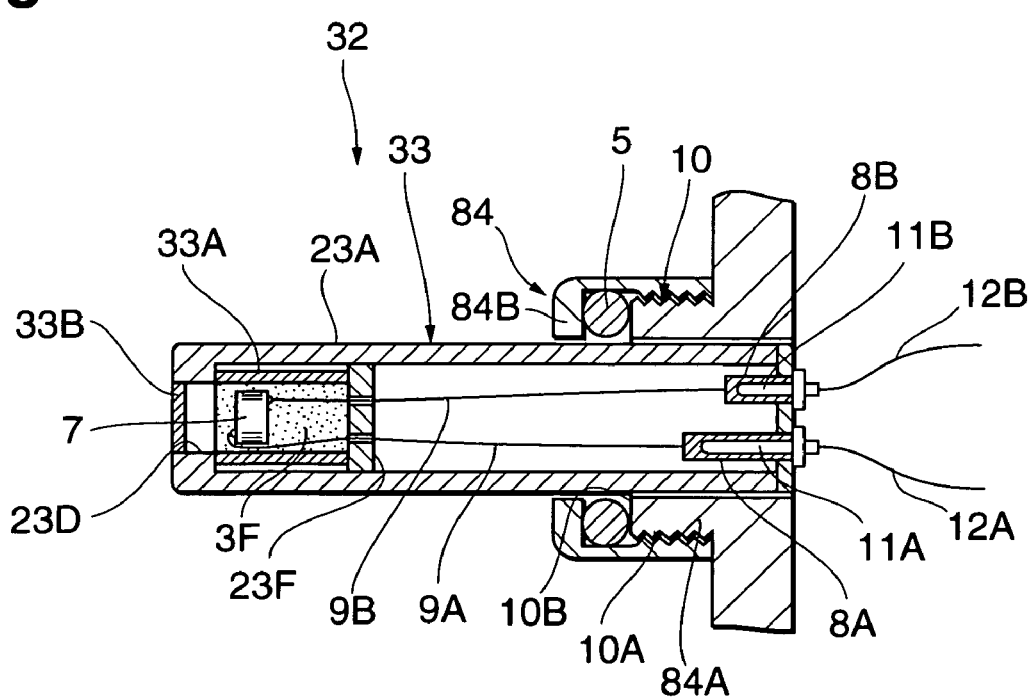
FIG. 15 is an enlarged sectional view showing a radiation detection probe according to a sixth embodiment.

The sixth embodiment is different from the second embodiment in the radiation detection probe and its mounting structure, and the other structures are configured in the same manner as in the second embodiment. A radiation detection probe 32 according to this embodiment has a detection unit 33 shown in FIG. 15 instead of the detection unit 23 (see FIG. 11) in the second embodiment. Furthermore, the radiation detection probe 32 has no probe cover.

The detection unit 33 has an element cover 33A instead of the element cover 23E shown in FIG. 11. The element cover 33A has the same shape as that of the element cover 23E. However, unlike the element cover 23E, the element cover 33A is made of a material, e.g., lead (Pb) or tungsten (W), which can block the radiation to be detected. Accordingly, like the side shield 6, the element cover 33A serves as a shield member which prevents sideward radiation from impinging upon the radiation detection element 7. Accordingly, the detection unit 33 does not have the side shield 6 built therein. The element cover 33A surrounds the radiation detection element 7 without contacting the radiation detection element 7.

Furthermore, the element cover 33A also serves as a collimator which collimates the radiation. The radiation detection element 7 is not disposed to be flush with the distal end of the element cover 33A but behind the distal end of the element cover 33A. In other words, the radiation detection element 7 is backwardly positioned by a certain distance from the distal end of the element cover 33A toward the proximal end of the element cover 33A. The portion of the element cover 33A placed at the front of the radiation detection element 7 not only prevents the sideward radiation from entering the radiation detection element 7 but also limits the frontward radiation incidence. As a result, only the radiation that travels substantially in parallel to the axis of the element cover 33A enters the radiation detection element 7. The radiation is collimated in this manner, thereby providing an enhanced directivity in the detection of radiation.

An input plate 33B is fitted into the distal end of the casing 23A so as to close an end of the reduced diameter portion 23D. The interface between the input plate 33B and the casing 23A is sealed. The input plate 33B functions in the same manner as the input plate 24B shown in FIG. 9. The input plate 33B is made of a material, e.g., aluminum or amorphous carbon, which blocks visible and infrared light but transmits the radiation. This is because incidence of electromagnetic waves other than the radiation to be detected upon the radiation detection element 7 generates noise signals. Preferably, the input plate 33B is made of a material which blocks electromagnetic waves having an energy of 1 keV or less. Other structures are the same as those of the detection unit 23, and thus detailed description will be omitted.

Since the detection unit 33 is sealed by the input plate 33B, the probe cover 24 shown in FIG. 9 is not required. That is, the radiation detection probe 32 according to this embodiment is configured of the detection unit 33 and the sockets 8A and 8B. In this embodiment, a coupling nut 84 replacing the probe cover 34, as a fastener for the detection unit 33, is mounted onto the proximal end portion of the element cover 33A. The detection unit 33 is fitted into the connector 10 and an internal thread 84A of the coupling nut 84 is screwed onto the external thread 10A of the connector 10, thereby attaching the detection unit 33 to the connector 10. At this time, the seal ring 5 is sandwiched between the distal end surface 10B of the connector 10 and a top wall 84B of the coupling nut 84 facing the distal end surface 10B. Consequently, the seal ring 5 is closely attached to the outer circumferential surface of the casing 23A, whereby the connector 10 and the main body 1 are sealed.

The input plate 33B seals the detection unit 33, while the seal ring 5 seals the main body 1. This allows the radiation detection probe according to this embodiment to be sterilized using a sterilizing gas such as EOG or washed in water. Also, it is possible to replace the radiation detection element 7 on a detection unit 33 basis by removing the coupling nut 64 from the connector 10.

Seventh Embodiment

Figure 16:
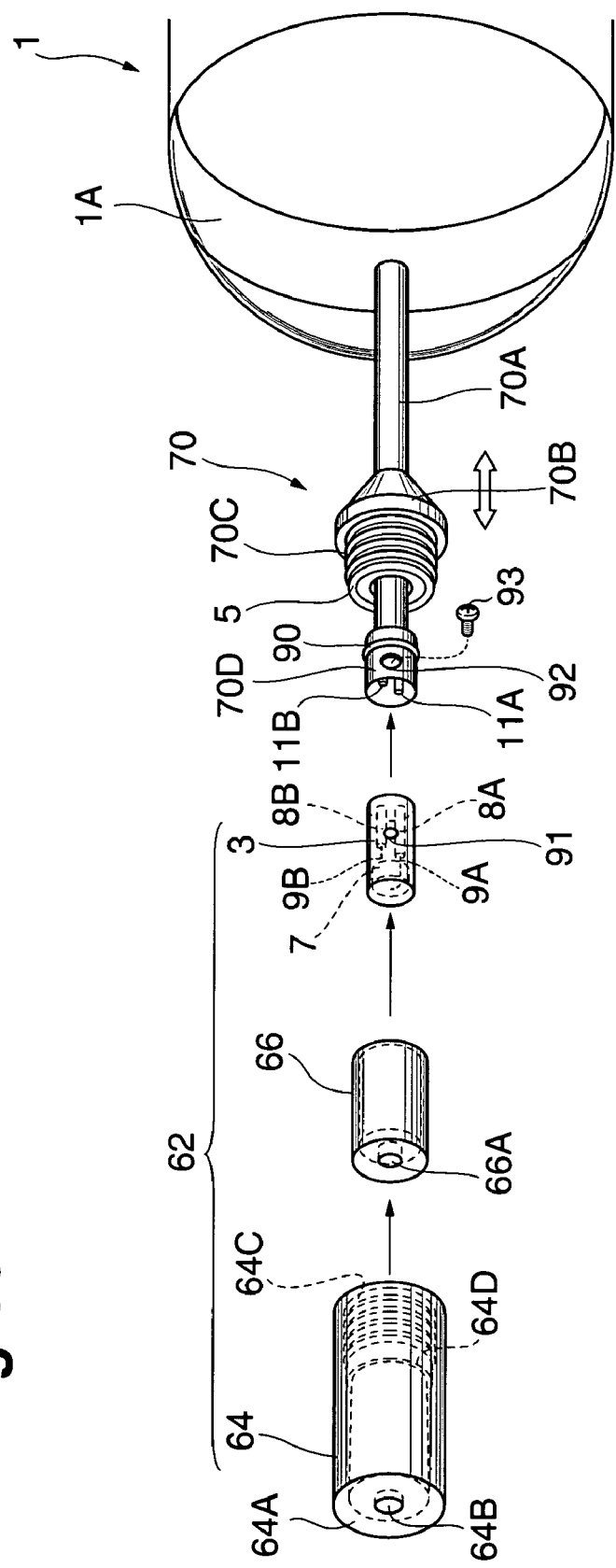
FIG. 16 is an exploded perspective view showing a radiation detection probe according to a seventh embodiment.

The seventh embodiment is different from the first and second embodiments in the radiation detection probe and its mounting structure, and the other structures are configured in the same manner as in those embodiments. As shown in FIG. 16, a radiation detection probe 62 has the detection unit 3, a probe cover 64, and a side shield 66. The detection unit 3 is housed in the side shield 66 which is in turn housed in the probe cover 64.

The probe cover 64 is formed in the shape of a cylindrical cap so as to cover the entirety of the side shield 66. For example, the probe cover 64 is made of a metal material such as stainless steel or aluminum or of an electrically conductive resin material. The probe cover 64 may be made of either a material which transmits the radiation to be detected or a material which blocks the radiation to be detected. At the center of a front wall 64A of the probe cover 4, there is formed an opening 64B which facilitates the transmission of the radiation. On the inner surface at the proximal end portion of the probe cover 64, there are formed an internal thread 64C used to mount the probe 2 to the main body 1 and an annular shoulder portion 64D for receiving the seal ring 5. The annular shoulder portion 64D is disposed adjacent to the distal end of the internal thread 64C.

The side shield 66 has a structure similar to that of the side shield 6 according to the first embodiment. However, the side shield 66 is longer than the side shield 6. The side shield 66 is made of a material, e.g., lead (Pb) or tungsten (W), which can block the radiation. The side shield 66 fits into the hollow portion of the probe cover 64. The hollow portion of the side shield 66 fits onto the detection unit 3. A radiation-introducing window 66A is perforated in the front wall of the side shield 66. The radiation enters the radiation detection element 7 through the window 66A. The side shield 66 prevents the sideward radiation from entering the radiation detection element 7. Also, the radiation-introducing window 66A serves as a collimator for the radiation.

The radiation detection probe 62 is detachably mounted to the distal end of the main body 1. The support member 1A disposed at the distal end of the main body 1 has a connector 70 to which the radiation detection probe 62 is detachably mounted. The connector 70 has an elongated support bar 70A which protrudes from the middle of the support member 1A. The support bar 70A is a cylindrical body extending coaxially with the main body 1 and has an outer diameter smaller than the outer diameter of the radiation detection probe 62. A connector main body 70B is attached to the middle portion of the support bar 70A. The support bar 70A passes through the main body 70B, and the main body 70B is able to slide relative to the support bar 70A. The front half portion of the main body 70B has an external thread 70C which screws into the internal thread 64C of the probe cover 64. The seal ring 5 is mounted to the distal end of the main body 70B adjacent to the external thread 70C. A cylindrical socket 70D which fits onto the detection unit 3 is provided on the distal end of the support bar 70A. The socket 70D has an outer diameter larger than the outer diameter of the support bar 70A. The detection unit 3 can be detachably fitted into the socket 70D. A groove into which a seal ring 90 is fitted is circumferentially formed on the side surface of the socket 70D. The terminal pins 11A and 11B are disposed in the opening of the socket 70D. These terminal pins are connected to a signal processing circuit (not shown) in the main body 1 via lead wires which extend inside the support bar 70A.

In this embodiment, a threaded hole 91 is provided in the side surface of the detection unit 3. Also, a through-hole 92 is provided in the side surface of the socket 70D. Inserting the detection unit 3 into the opening of the socket 70D will allow the threaded hole 91 and the through-hole 92 to be aligned. A screw 93 can be screwed into the threaded hole 91 and the through-hole 92.

As shown in FIG. 16, since the connector 70 has the external thread 70C, the proximal end portion of the probe cover 64 can be fastened to the connector 70. After fastening the proximal end portion, the seal ring 5 is sandwiched and held between the distal end surface 10B of the connector 10 and the annular shoulder portion 64C of the probe cover 64.

To mount the radiation detection probe 62 to the distal end of the main body 1, the detection unit 3 is first inserted into the connector 70D, thereby inserting the terminal pins 11A and 11B into the sockets 8A and 8B. Thereafter, the screw 93 is screwed into the threaded hole 91 and the through-hole 92 to tightly fix the detection unit 3 to the socket 70D. The seal ring 90 is also mounted to the socket 70D. Then, the seal ring 5 is mounted to the connector 70 and the side shield 66 is fitted into the distal end portion of the probe cover 64. Subsequently, the probe cover 64 is attached to the connector 70 so that the detection unit 3 is inserted into the side shield 66, and the internal thread 64C of the probe cover 64 is engaged with the external thread 70C of the connector 70. This causes the seal ring 5 to be sandwiched between the distal end surface of the connector 70 and the annular shoulder portion 64C of the probe cover 64. The seal ring 90 is also sandwiched between the outer surface of the socket 70D and the inner surface of the side shield 66. This simple procedure allows the cap-shaped probe cover 64 to be mounted to the connector 70 so as to cover the side shield 66 and the detection unit 3.

When the radiation detection probe 62 is mounted to the connector 70, the probe cover 64 and the side shield 66 are able to slide along with the connector main body 70B relative to the support bar 70A. On the other hand, the detection unit 3 mounted to the socket 70D cannot move relative to the support bar 70A. Accordingly, sliding the radiation detection probe 62 will cause the side shield 66 to move relative to the detection unit 3 along the axis of the probe 62. However, during this movement, the radiation detection element 7 always stays within the side shield 66.

Since the detection unit 3 is attached to the socket 70D by the screw, the detection unit 3 will never fall off from the socket 70D while the side shield 66 is sliding. The seal ring 90 sandwiched between the side shield 66 and the socket 70D not only seals the radiation detection element 7 but also serves as an anti-skidding means while the side shield 66 is sliding.

This embodiment also has an advantage that the orientation of the radiation detection probe 62 can be readily determined because the probe 62 is connected to the main body 1 via the elongated support bar 70A. According to the first to the sixth embodiments, the radiation detection probe larger in diameter than the support bar 70A is directly connected to the main body 1. Hence, when the user grasps the main body to direct the probe toward a place to be measured, the proximal end portion of the probe can obstruct the line of sight, thereby obscuring the distal end of the probe. In contrast to this, according to this embodiment, the support bar 70A which is thinner than the radiation detection probe 62 is provided between the probe 62 and the main body 1, thereby allowing the distal end of the radiation detection probe 62 to be readily viewed. Accordingly, the user can readily determine the orientation of the probe 62, thereby smoothly proceeding with the detection of the radiation.

Furthermore, sliding the main body 70B along the support bar 70A makes it possible to readily position the radiation-introducing window 66A, which is a collimator, closer to or farther away from the radiation detection element 7. Consequently, it is possible to easily adjust the sensitivity of the radiation detection element 7.

Eighth Embodiment

Figure 17:
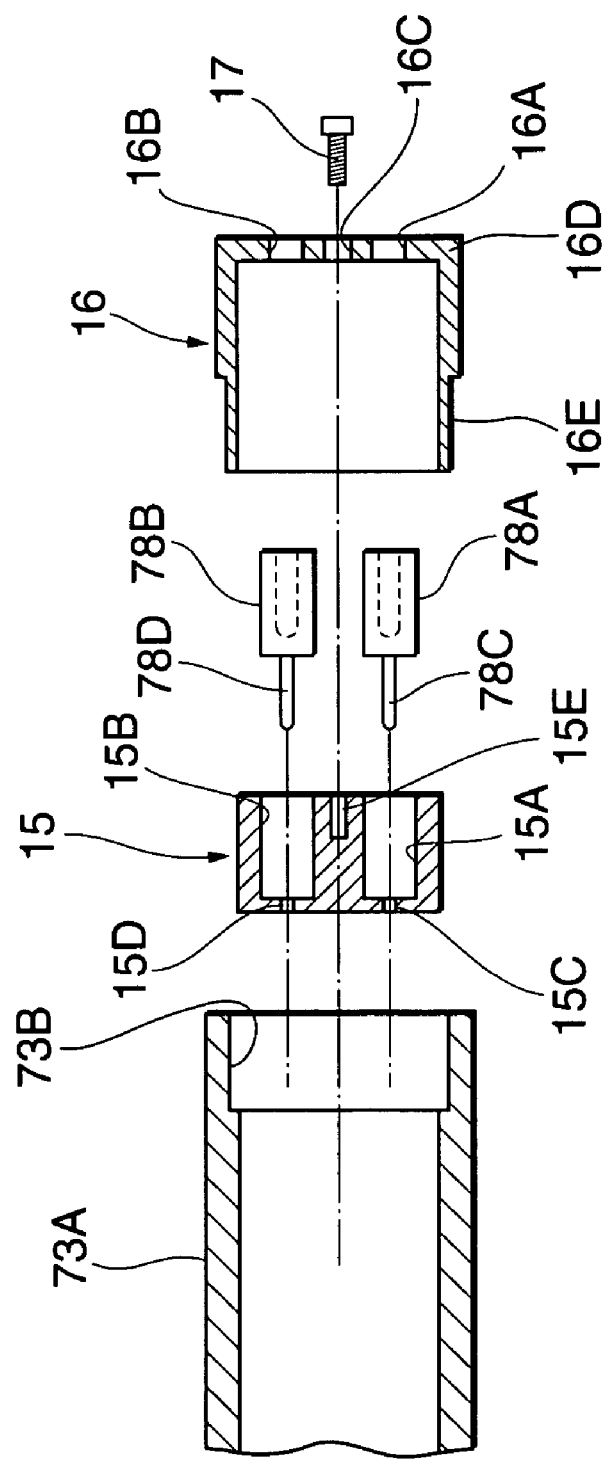
FIG. 17 is an exploded sectional view showing a modified example of a fixing structure for a socket according to an eighth embodiment.
Figure 18:
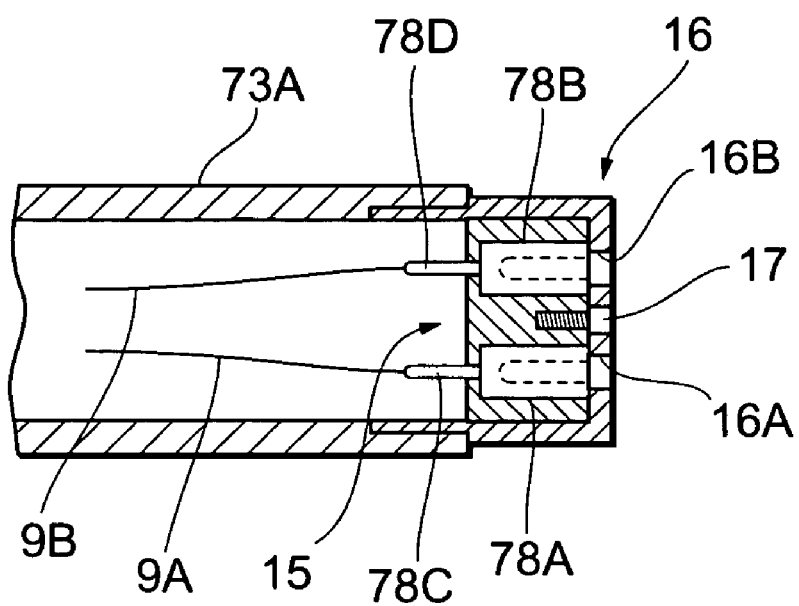
FIG. 18 is a sectional view showing the assembled fixing structure for the socket according to the eighth embodiment.

The eighth embodiment is different from the first embodiment in the fixing structure of a socket for a terminal pin, and the other structures are configured in the same manner as in the first embodiment. As shown in FIG. 17 and FIG. 18, sockets 78A and 78B to be employed in this embodiment are fixed to the proximal end of a casing 73A using a socket fixture member 15 and a socket cover 16 instead of the support plate 3E shown in FIG. 6.

The casing 73A is different from the casing 3A only in the structure of the proximal end, and the other structures are configured in the same manner as those of the casing 3A. The casing 73A has an opening 73B at its proximal end for receiving the distal end of the socket cover 16. The casing 73A may be composed either of a material which transmits the radiation to be detected or a material which blocks the radiation to be detected.

The socket fixture member 15 is an approximately cylindrical column and made of an electrically highly insulating material. In one end face of the socket fixture member 15, socket accommodating holes 15A and 15B are perforated into which the socket 78A and 78B are fitted. At the center of the end face, a threaded hole 15E used to fasten the socket cover 16 is formed. In the opposite end face of the socket fixture member 15, through-holes 15C and 15D are perforated which have the diameters smaller than those of the socket accommodating holes 15A and 15B. When sockets 68A and 68B are inserted into the socket accommodating holes 15A and 15B, connection pins 78C and 78D that protrude from the ends of the sockets 8A and 8B will penetrate the through-holes 15C and 15D.

The socket cover 16 is formed in the shape of a cap so as to cover the socket fixture member 15. In an upper wall 16D of the socket cover 16, through-holes 16A and 16B corresponding to the sockets 8A and 8B are provided. When the sockets 8A and 8B are fitted into the socket accommodating holes 15A and 15B, the sockets 8A and 8B will face the through-holes 16A and 16B. At the center of the upper wall 16D, there is also formed a through-hole 16C for a set screw 17. The set screw 17 is screwed into the threaded hole 15E of the socket fixture member 15 through the hole 16C. As shown in FIG. 17, the socket cover 16 receives the socket fixture member 15, and is fixed to the socket fixture member 15 using the set screw 17. The socket cover 16 has a spigot 16E at its distal end. The spigot 16E is fitted into the opening 73B of the casing 73A and adhered to the casing 73A.

In the foregoing, the present invention has been described in detail in accordance with the embodiments. However, the present invention is not limited to the above-mentioned embodiments. Various modifications can be made to the present invention without deviating from the scope of the invention.

In the first to seventh embodiments, the detection unit includes the sockets 8A and 8B for terminal pins having different fitting lengths, however, instead of this, the detection unit may include sockets having an equal fitting length. The main body 1 includes the terminal pins 11A and 11B having different fitting lengths, however, instead of this, the main body 1 may include terminal pins having an equal fitting length. Furthermore, the detection unit may be provided with a terminal pin, while the connector of the main body may be provided with a socket for the terminal pin.

The distal end portion of the radiation detection probe 2 shown in FIG. 5 and the radiation detection probe 22 shown in FIG. 10 is not limited to a planar shape, and may be a rounded shape such as a spherical shape.

In the radiation detector 100 shown in FIG. 1, the radiation detection probe 2 is mounted while being inclined with respect to the axis of the main body 1. However, the radiation detection probe 2 may be mounted to protrude along the axis of the main body 1. Furthermore, the ratio between the diameter and the length of the radiation detection probe 2 is not limited to those in the examples shown in the figures, and may be modified as appropriate.

The radiation detector according to the above-mentioned embodiments is a medical surgical probe; however, the use of the radiation detector of the present invention is not limited thereto, and the radiation detector of the present invention may be employed in a wide range of other applications.

INDUSTRIAL APPLICABILITY

The radiation detector in accordance with the present invention collimates radiation from a place to be measured and introduce the radiation to the radiation detection element. This makes it possible to detect the dose of the radiation from the place to be measured with high accuracy. Furthermore, since the detection unit having the radiation detection element is detachably attached to the connector of the main body, it is possible to replace the radiation detection element with simple operation.

The invention claimed is:

1. A radiation detector comprising:
   a main body;
   a radiation probe detachably attached to the main body; and
   a collimator for collimating radiation, the collimator being provided in the distal end portion of the radiation detection probe,
   the radiation detection probe having: a detection unit including a radiation detection element; a first terminal electrically connected to the radiation detection element; and a cap-shaped shield member mounted to the detection unit so as to cover the radiation detection element, the shield member being made of a material which blocks the radiation, the shield member having a front wall facing the radiation detection element, and a cylindrical side wall extending from the edge of the front wall, the collimator being a through-hole provided in the front wall,
   the main body having a connector to which the proximal end of the radiation detection probe is detachably mounted, the connector including a second terminal which is detachably connected to the first terminal when the radiation detection probe is mounted to the connector,
   the radiation detection probe further having:
   a cap-shaped probe cover which covers the shield member and the detection unit, the probe cover being detachably mounted to the connector; and
   a seal ring sandwiched between the probe cover and the connector to seal the main body and the radiation detection probe when the probe cover is mounted to the connector.

2. A radiation detector according to claim 1, wherein
the detection unit has an input face which faces the collimator and transmits the radiation, and
the radiation detection element is arranged so as to receive the radiation which has passed through the input face.

3. A radiation detector according to claim 1, wherein
the shield member is disposed in the probe cover to allow a hollow portion of the shield member and a hollow portion of the probe cover to communicate with each other, and
the detection unit is fitted into these hollow portions which communicate with each other.

4. A radiation detector according to claim 3, wherein the shield member is detachably provided in the probe cover.

5. A radiation detector according to claim 3, wherein the shield member is fixed in the probe cover.

6. A radiation detector according to claim 1, wherein
the probe cover has a cap-shaped first component detachably mounted to the connector, a cap-shaped second component detachably attached to the first component to accommodate and fix the shield member, and a seal ring sandwiched between the outer surface of the first component and the inner surface of the second component to seal the probe cover when the second component is attached to the first component, and
the second component is attached at positions variable along the axis of the probe cover.

7. A radiation detector according to claim 1, wherein
the probe cover has an input plate facing the front wall of the shield member to close an end of the collimator, and a cylindrical side wall extending from the edge of the input plate to surround the side surfaces of the shield member and the detection unit, and
the input plate is made of a material which transmits the radiation and blocks an electromagnetic wave having an energy of 1 keV or less.

8. A radiation detector according to claim 1, wherein
the detection unit has a casing for accommodating the radiation detection element,
an opening is provided on the distal end of the casing so as to extend from an end face of the casing toward the radiation detection element, and
the opening has substantially the same cross-section as that of the collimator and communicates with the collimator.

9. A radiation detector comprising:
a main body;
a radiation detection probe detachably attached to the main body; and
a collimator for collimating radiation, the collimator being provided in the distal end portion of the radiation detection probe,
the radiation detection probe having a detection unit including a radiation detection element, and a first terminal electrically connected to the radiation detection element,
the main body having a connector to which the proximal end of the radiation detection probe is detachably mounted, the connector including a second terminal which is detachably connected to the first terminal when the radiation detection probe is mounted to the connector,
the radiation detection probe further having:
a cap-shaped probe cover which covers the detection unit, the probe cover being detachably mounted to the connector; and
a seal ring sandwiched between the probe cover and the connector to seal the main body and the radiation detection probe when the probe cover is mounted to the connector,
the probe cover being made of a material which blocks the radiation,
the collimator being an opening provided on the distal end of the probe cover to extend toward the radiation detection element,
the radiation detector further comprising an input plate for closing an end of the collimator, the input plate being provided on the distal end surface of the probe cover, and the input plate being made of a material which transmits the radiation and blocks an electromagnetic wave having an energy of 1 keV or less.

10. A radiation detector according to claim 9, wherein
the detection unit has an input face which faces the collimator and transmits the radiation, and
the radiation detection element is arranged so as to receive the radiation which has passed through the input face.

11. A radiation detector comprising:
a main body;
a radiation detection probe detachably attached to the main body; and
a collimator for collimating radiation, the collimator being provided in the distal end portion of the radiation detection probe,
the radiation detection probe having a detection unit including a radiation detection element, and a first terminal electrically connected to the radiation detection element,
the main body having a connector to which the proximal end of the radiation detection probe is detachably mounted, the connector including a second terminal which is detachably connected to the first terminal when the radiation detection probe is mounted to the connector,
the connector further including a support bar protruding from the distal end of the main body and being thinner than the radiation detection probe, and
the support bar having a proximal end connected to the distal end of the main body and a distal end connected to the radiation detection probe.

12. A radiation detector according to claim 11, wherein
the detection unit has an input face which transmits the radiation,
the radiation detection element is arranged so as to receive the radiation which has passed through the input face, and
the collimator is an opening which faces the input face.

13. The radiation detector according to claim 11, wherein
the connector further includes a slide member slidably attached to the support bar, and
the collimator moves along with the slide member, and the distance between the collimator and the radiation detection element varies went the slide member slides relative to the support bar.

14. A radiation detector comprising:
a main body;
a radiation detection probe detachably attached to the main body; and
a collimator for collimating radiation, the collimator being provided in the distal end portion of the radiation detection probe, the radiation detection probe having a detection unit including a radiation detection element, and a first terminal electrically connected to the radiation detection element, the main body having a connector to which the proximal end of the radiation detection probe is detachably mounted, the connector including a second terminal which is detachably connected to the first terminal when the radiation detection probe is mounted to the connector, one of the first and second terminals including a plurality of pins having different fitting lengths and different polarities, and the other including a plurality of sockets into which the plurality of pins are fitted, the plurality of sockets having fitting lengths and polarities corresponding to the plurality of pins.

15. A radiation detector according to claim 14, wherein the detection unit has an input face which transmits the radiation, the radiation detection element is arranged so as to receive the radiation which has passed through the input face, and the collimator is an opening which faces the input face.

16. A radiation detector comprising a main body, and a radiation detection probe detachably attached to the main body, the radiation detection probe having a radiation detection element, a first terminal electrically connected to the radiation detection element, a cylindrical element cover surrounding the radiation detection element, and a cylindrical casing for accommodating the element cover, the main body having a connector to which the proximal end of the radiation detection probe is detachably mounted, the connector including a second terminal which is detachably connected to the first terminal when the radiation detection probe is mounted to the connector, the element cover being made of a material which blocks radiation, and the radiation detection element being disposed behind the distal end of the element cover.

17. A radiation detector according to claim 16, further comprising a fastener detachably mounted to the main body to fasten the radiation detection probe to the connector.

18. A radiation detector according to claim 17, further comprising a seal ring sandwiched between the fastener and the connector to seal the main body when the fastener is mounted to the connector.

19. A radiation detector according to claim 16, wherein an input plate facing the radiation detection element is provided on the distal end surface of the casing, and the input plate is made of a material which transmits the radiation and blocks an electromagnetic wave having an energy of 1 keV or less.

* * * * *